(12) United States Patent
Abada et al.

(10) Patent No.: US 10,766,961 B2
(45) Date of Patent: Sep. 8, 2020

(54) ANTI-VEGFR2 ANTIBODY THERAPY FOR HEPATOCELLULAR CARCINOMA

(71) Applicant: IMCLONE, LLC, Indianapolis, IN (US)

(72) Inventors: Paolo B. Abada, Indianapolis, IN (US); Shao-Chun Chang, Carmel, IN (US); Yanzhi Hsu, Basking Ridge, NJ (US); Ling Yang, Bridgewater, NJ (US)

(73) Assignee: ImClone LLC, Indianapolis, IN (US)

( * ) Notice: Subject to any disclaimer, the term of this patent is extended or adjusted under 35 U.S.C. 154(b) by 70 days.

(21) Appl. No.: 15/501,507

(22) PCT Filed: Aug. 11, 2015

(86) PCT No.: PCT/US2015/044632
§ 371 (c)(1),
(2) Date: Feb. 3, 2017

(87) PCT Pub. No.: WO2016/025464
PCT Pub. Date: Feb. 18, 2016

(65) Prior Publication Data
US 2017/0226212 A1 Aug. 10, 2017

Related U.S. Application Data

(60) Provisional application No. 62/037,848, filed on Aug. 15, 2014.

(51) Int. Cl.
| | | |
|---|---|---|
| *G01N 33/574* | (2006.01) | |
| *A61K 39/395* | (2006.01) | |
| *C07K 16/28* | (2006.01) | |
| *C07K 16/30* | (2006.01) | |
| *A61P 35/00* | (2006.01) | |
| *A61K 39/00* | (2006.01) | |

(52) U.S. Cl.
CPC .......... *C07K 16/2863* (2013.01); *A61P 35/00* (2018.01); *G01N 33/57438* (2013.01); *A61K 39/395* (2013.01); *A61K 2039/505* (2013.01); *A61K 2039/545* (2013.01); *A61K 2039/55* (2013.01); *C07K 2317/21* (2013.01); *G01N 2333/47* (2013.01); *G01N 2800/52* (2013.01)

(58) Field of Classification Search
CPC ............. G01N 33/574; G01N 2800/52; G01N 2800/54; G01N 2800/56; A61K 39/395
See application file for complete search history.

(56) References Cited

U.S. PATENT DOCUMENTS

2012/0214830 A1* 8/2012 Buck ................ G01N 33/57438
514/266.4

FOREIGN PATENT DOCUMENTS

| WO | 2003/075840 A2 | 9/2003 |
| WO | 2012/116040 A1 | 8/2012 |

OTHER PUBLICATIONS

Zhu et al., Clin Cancer Res, 2013, 19(23):6614-23.*
Huang et al., J Clin Pathol, 2011, 64:343-348.*
Clinical Trial NCT01140347, A study of ramucirumab (IMC-1121B) drug product (DP) and best supportive care (BSC) versus placebo and BSC as 2nd line treatment in participants with hepatocellular carcinoma after 1st-line therapy with sorafenib, Jun. 9, 2010.*
Shao et al., Caner, 2010, 116:4590-6.*
McIntire et al., Cancer Res., 1975, 35: 991-996.*
Kaseb et al., Cancer, 2011, 117(11): 1-21.*
Ann-Lii Cheng et al; "Efficacy and Safety of sorafenib in patients with advanced hepatocellular carcinoma according to baseline status: Subset analyses of the phase III Sorafenib Asia-Pacific trial", European Journal of Cancer, vol. 48, No. 10, Jan. 10, 2012.
A.X. Zhu et al, "A Phase II and Biomarker Study of Ramucirumab, a Human Monoclonal Antibody Targeting the VEGF Receptor-3, as First Line Monotherapy in Patients with Advanced Hepatocellular Cancer", Clinical Cancer Research. vol. 19, No. 23, Dec. 1, 2013.
Andrew X Zhu et al: "Ramucirumab versus placebo as second-line treatment I patients with advanced hepatocellular carcinoma following first-line therapy with sorafenib (REACH): a randomized, double-blind, multicenter, phase 3 trial", Lacent Oncology, vol. 16, Jun. 19, 2015.
Alejandro Forner et al: "Does Ramucirumab deserve a second chance for liver cancer?" Lancet Oncology, vol. 16, No. 7, Jul. 1, 2015.
Jean-Luc Raoul et al: "Using Modified RECIST and Alpha-Fetoprotein Levels to Assess Treatment Benefit in Hepatocellular Carcinoma", Liver Cancer, vol. 3, No. 3-4, Aug. 15, 2014.
Lu, Dan et al: "Tailoring in Vitro Selection for a Picomolar Affinity Human Antibody Directed against Vascular Endothelial Growth Factor Receptor 2 for Enhanced Neutralizing Activity", The Journal of Biological Chemistry, vol. 278, No. 44, 2003, pp. 43496-43507.
Lu, Dan et al: "Selection of High Affinity Human Neutralizing Antibodies to VEGFR2 From a large antibody phage display library for antiangiogenesis therapy", Int. J. Cancer: 97, 393-399 (2002).
Hua-Quan Miao et al: "Potent neutralization of VEGF biological activities with a fully himan antibody Fab fragment directed against VEGF receptor 2", Biochemical and Biophysical Research Communications 345 (2006) 438-445.
Ax Zhu et al: "A Phase 2 study of Ramucirumab(IMC-1121B) as First-line Monotherapy in Patients (pts) with Advanced Hepatocellular Carcinoma (HCC) (CP12-0710/NCT00627042)", Massachusetts General Hospital Cancer Center, Harvard medical School, Boston, MA; ASCO May 27, 2010.

(Continued)

*Primary Examiner* — Hong Sang
(74) *Attorney, Agent, or Firm* — Margaret Tomaska

(57) ABSTRACT

The invention provides for a human antibody that binds to human vascular endothelial growth factor receptor 2, preferably ramucirumab, for the treatment of hepatocellular carcinoma (HCC) in patients having levels of alpha-fetoprotein (AFP) of 1.5×ULN (Upper Limit of Normal) or greater, and as a predictive method for the treatment of HCC in patients having AFP levels of 1.5×ULN or greater.

20 Claims, No Drawings
Specification includes a Sequence Listing.

(56) References Cited

OTHER PUBLICATIONS

H. Wilke, et al: RAINBOW: A Global, Phase 3, Randomized, Double-Bling Trial of Ramucirumab and Paclitaxel (PAC) Versus Placebo and PAC in the Treatment of Metastatic Gastric or Gastroesophageal Junction (GEJ) Adenocarcinoma Following Disease Progression on First-Line Platinum- and Flutopyrimidine-Containing Combination Therapy, ASCO GI 2014 Poster.

H. Wilke, et al: RAINBOW: A Global, Phase 3, Randomized, Double-Bling Trial of Ramucirumab and Paclitaxel (PAC) Versus Placebo and PAC in the Treatment of Metastatic Gastric or Gastroesophageal Junction (GEJ) Adenocarcinoma Following Disease Progression on First-Line Platinum- and Flutopyrimidine-Containing Combination Therapy, ASCO GI 2014 Presentation.

Ferlay J, Soerjomataram I, Ervik M, Dikshit R, Eser S, Mathers C, Rebelo M, Parkin DM, Forman D, Bray, F.GLOBOCAN 2012 v1.0, Cancer Incidence and Mortality Worldwide: IARC CancerBase No. 11 [Internet]. Lyon, France: International Agency for Research on Cancer; 2013.Accessed on Jun. 10, 2014.

Bruix, et al., J Hepatology 57:821-829 (2012).

Johnson, et al.,J Clin Oncol 31(28) :3517-3524, 3521 (2013).

Cheng, et al., J Clin Oncol, ASCO Annual Mtf Abstr Part 1, vol. 29, No. 15 suppl 9May 20 Supplement) 2011:4000.

Llovet, Clin Can Res, Mar. 3, 2014, 1-20.

Llovet , et al., J Clin Onc 31(28):3509-3516 (2013).

European Association for the Study of the Liver, European Organisation for Research and Treatment of Cancer, Journal of Hepatology 56:908-943, 919 (2012).

Chothia, et al., J Mol Biol. 196:901-917 (1987).

* cited by examiner

SEQUENCE LISTING

```
<160> NUMBER OF SEQ ID NOS: 2

<210> SEQ ID NO 1
<211> LENGTH: 446
<212> TYPE: PRT
<213> ORGANISM: Artificial Sequence
<220> FEATURE:
<223> OTHER INFORMATION: Synthetic

<400> SEQUENCE: 1

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Ile Trp Gly Gln Gly Thr Met Val
            100                 105                 110

Thr Val Ser Ser Ala Ser Thr Lys Gly Pro Ser Val Leu Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270
```

```
Lys Phe Asn Trp Tyr Val Asp Gly Val Glu Val His Asn Ala Lys Thr
            275                 280                 285
Lys Pro Arg Glu Glu Gln Tyr Asn Ser Thr Tyr Arg Val Val Ser Val
        290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 2
<211> LENGTH: 214
<212> TYPE: PRT
<213> ORGANISM: Artificial Sequence
<220> FEATURE:
<223> OTHER INFORMATION: Synthetic

<400> SEQUENCE: 2

Asp Ile Gln Met Thr Gln Ser Pro Ser Ser Val Ser Ala Ser Ile Gly
1               5                   10                  15
Asp Arg Val Thr Ile Thr Cys Arg Ala Ser Gln Gly Ile Asp Asn Trp
            20                  25                  30
Leu Gly Trp Tyr Gln Gln Lys Pro Gly Lys Ala Pro Lys Leu Leu Ile
        35                  40                  45
Tyr Asp Ala Ser Asn Leu Asp Thr Gly Val Pro Ser Arg Phe Ser Gly
    50                  55                  60
Ser Gly Ser Gly Thr Tyr Phe Thr Leu Thr Ile Ser Ser Leu Gln Ala
65                  70                  75                  80
Glu Asp Phe Ala Val Tyr Phe Cys Gln Gln Ala Lys Ala Phe Pro Pro
                85                  90                  95
Thr Phe Gly Gly Gly Thr Lys Val Asp Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205
Phe Asn Arg Gly Glu Cys
        210
```

ANTI-VEGFR2 ANTIBODY THERAPY FOR HEPATOCELLULAR CARCINOMA

This application claims the benefit of U.S. Provisional Application No. 62/037,848 which was filed 15 Aug. 2014.

This invention is directed to the field of cancer treatment. More specifically, the present invention is directed to ramucirumab to treat hepatocellular carcinoma (HCC) in patients having high levels of alpha-fetoprotein (AFP), and as a medicament for the treatment of HCC in patients having high levels of AFP.

Liver cancer is the sixth most commonly diagnosed cancer worldwide and the second most common cause of cancer death. HCC represents approximately 90% of primary liver cancers. HCC is often diagnosed at an advanced stage, and common treatment options such as hepatic resection, liver transplantation, and percutaneous ablation, have limited usefulness, with 70% of patients having recurrent disease within 5 years and reaching a more advanced tumor stage. (Bruix, et al., J Hepatology 57:821-829 (2012)).

Sorafenib is the only approved systemic drug for the treatment of advanced HCC and is the standard of care. (Bruix, supra.) There have been at least six failed phase III clinical trials in first and second line HCC. (Johnson, et al., J Clin Oncol 31(28):3517-3524, 3521 (2013); Cheng, et al., J Clin Oncol, ASCO Annual Mtg Abstr Part 1, Vol 29, No 15 suppl (May 20 Supplement) 2011:4000; Llovet, Clin Can Res, Mar. 3, 2014, 1-20); Llovet, et al., J Clin Onc 31(28): 3509-3516 (2013)).

AFP is a glycoprotein that is produced by a variety of tumors. Serum AFP is the most widely studied screening test for detecting HCC. The normal range for serum AFP levels is 1-10 ng/mL. AFP serum levels of greater than 200 ng/mL and/or 400 ng/mL have been correlated with poor prognosis in HCC patients. In particular, increased serum concentrations of AFP have been shown to be a prognostic factor for mortality in patients with HCC. (European Association for the Study of the Liver, European Organisation for Research and Treatment of Cancer, Journal of Hepatology 56:908-943, 919 (2012); Johnson, supra.)

WO2012/116040 discloses that HCC cell lines that possess high AFP are more sensitive to growth inhibition by OSI-906, an IGF-1R kinase inhibitor. No data from human patients has been reported that supports the contention that HCC patients having high levels of AFP respond to treatment with OSI-906.

Ramucirumab (also "IMC-1121B"), CAS registry number 947687-13-0, is a fully human monoclonal antibody directed against the vascular endothelial growth factor receptor 2 (VEGFR2 or VEGF receptor-2).

Ramucirumab and methods of making and using this compound, including for the treatment of neoplastic diseases such as solid and non-solid tumors, are disclosed in WO2003/075840 and all patents granted therefrom. Furthermore, clinical activity for ramucirumab has been reported in a Phase II study of patients with advanced hepatocellular cancer. (Zhu, et al., Clin. Cancer Res; 19(23):6614-6623 (2013).) AFP was not used as a predictive marker in this Phase II study.

There remains a need for treatments for advanced HCC and methods of predicting patient response to treatment for advanced HCC.

The present invention is derived from a Phase 3 clinical trial of the anti-VEGFR2 antibody, ramucirumab ("A Multicenter, Randomized, Double-Blind, Phase 3 Study of Ramucirumab (IMC-1121B) Drug Product and Best Supportive Care (BSC) Versus Placebo and BSC as Second-Line Treatment in Patients with Hepatocellular Carcinoma Following First-Line Therapy With Sorafenib") (the "Study").

It has surprisingly been found that HCC patients with AFP serum levels greater than or equal to 1.5 times the upper limit of normal (ULN) received an unexpected survival benefit of three months from treatment with ramucirumab as compared to treatment with placebo.

The method of treatment of the invention unexpectedly provides a method for using AFP serum levels as a predictive selection marker for the treatment of patients with advanced HCC with ramucirumab.

It has surprisingly been found that HCC patients with AFP serum levels greater than or equal to 1.5×ULN respond to treatment with ramucirumab, whereas patients with AFP serum levels less than 1.5×ULN do not respond to treatment with ramucirumab.

Neither the patent disclosure of WO2003/075840 nor the clinical trial Study design provide any suggestion of the role of targeting patients who have high AFP serum levels for the treatment with ramucirumab.

According to the first aspect of the present invention there is ramucirumab for use in the treatment of a hepatocellular tumor, wherein the patient has an alpha-fetoprotein level of 1.5 times the upper limit of normal or greater.

Another aspect of the invention is ramucirumab for use in treating a hepatocellular tumor, comprising the steps of: (1) assaying a sample from a patient for alpha-fetoprotein, (2) determining the level of alpha-fetoprotein in the sample, and (3) administering ramucirumab to the patient if alpha-fetoprotein is present at a level of 1.5 times the upper limit of normal or greater.

Another aspect of the invention is the use of ramucirumab in the manufacture of a medicament for the treatment of a patient with a hepatocellular tumor, wherein the patient has an alpha-fetoprotein level of 1.5 times the upper limit of normal or greater.

Another aspect of the invention is an in vitro method of selecting a patient having a hepatocellular tumor for treatment with a therapeutically effective amount of ramucirumab, comprising assaying for the presence of alpha-fetoprotein in a sample taken from the patient, wherein the patient is selected for treatment with ramucirumab if alpha-fetoprotein is present in the sample at a level of 1.5 times the upper limit of normal or greater.

Another aspect of the invention is a method of identifying a hepatocellular tumor patient eligible for treatment with ramucirumab, comprising assaying for the presence of alpha-fetoprotein in a sample taken from the patient prior to the administration of a therapeutically effective amount of ramucirumab, wherein the patient is eligible for treatment with ramucirumab if the alpha-fetoprotein level is 1.5 times the upper limit of normal or greater.

In another preferred aspect of the invention, the sample is plasma or serum.

Another aspect of the invention is a therapeutic regimen for treating a patient with a hepatocellular tumor, comprising: (1) assaying for the presence of alpha-fetoprotein in a sample taken from a patient, (2) selecting the patient for treatment with ramucirumab if alpha-fetoprotein is present in the sample at a level of 1.5 times the upper limit of normal or greater, and (3) administering ramucirumab to the patient.

Another aspect of the invention is a therapeutic regimen for treating a hepatocellular tumor, comprising: (1) assaying for the presence of alpha-fetoprotein in a sample taken from a patient, (2) selecting a patient for treatment with ramucirumab if alpha-fetoprotein is present in the sample at a level of 1.5 times the upper limit of normal or greater, and (3) administering ramucirumab to the selected patient.

Another aspect of the invention is a pharmaceutical composition comprising ramucirumab with one or more pharmaceutically acceptable carriers, diluents, or excipients, for use in the treatment of a patient having a hepatocellular tumor with ramucirumab, wherein the patient has an alpha-fetoprotein level of 1.5 times the upper limit of normal or greater.

Another aspect of the invention, there is a method of treating a hepatocellular tumor in a patient, comprising administering a therapeutically effective amount of ramucirumab to the patient in need thereof, provided that the patient is selected for treatment on the basis of a sample taken from the patient that has an alpha-fetoprotein level of 1.5 times the upper limit of normal or greater.

Another aspect of the invention is a method of predicting the response of a hepatocellular tumor patient to treatment with ramucirumab, comprising assaying a sample taken from the patient to determine the presence of alpha-fetoprotein in the sample, wherein the presence of an alpha-fetoprotein level of 1.5 times the upper limit of normal or greater is predictive of the patient's effective response to treatment with ramucirumab.

Another aspect of the invention is a method of treating a hepatocellular tumor in a patient, comprising administering a therapeutically effective amount of ramucirumab to the patient in need thereof, provided that a sample taken from the patient has an alpha-fetoprotein level of 1.5 times the upper limit of normal or greater.

Another aspect of the invention is a method of treating a hepatocellular tumor in a patient, comprising assaying a sample taken from the patient for alpha-fetoprotein prior to administering ramucirumab, and administering to the patient a therapeutically effective amount of ramucirumab if the sample has an alpha-fetoprotein level of 1.5 times the upper limit of normal or greater.

Another aspect of the invention is an improved method of treating a patient having a hepatocellular tumor with ramucirumab, the method comprising determining the presence of alpha-fetoprotein in a sample taken from the patient, and wherein the level of alpha-fetoprotein is determined prior to administration of a therapeutically effective amount of ramucirumab, and wherein the patient is selected for treatment with ramucirumab if the alpha-fetoprotein level is 1.5 times the upper limit of normal or greater.

In another preferred aspect of the invention, the alpha-fetoprotein level is 10 ng/mL or greater.

In another preferred aspect of the invention, the alpha-fetoprotein level is 15 ng/mL or greater.

In another preferred aspect of the invention, the alpha-fetoprotein level is 20 ng/mL or greater.

In another preferred aspect of the invention, the alpha-fetoprotein level is 30 ng/mL or greater.

In another preferred aspect of the invention, the alpha-fetoprotein level is 40 ng/mL or greater.

In another preferred aspect of the invention, the alpha-fetoprotein level is 50 ng/mL or greater.

In another preferred aspect of the invention, the alpha-fetoprotein level is 60 ng/mL or greater.

In another preferred aspect of the invention, the alpha-fetoprotein level is 70 ng/mL or greater.

In another preferred aspect of the invention, the alpha-fetoprotein level is 80 ng/mL or greater.

In another preferred aspect of the invention, the alpha-fetoprotein level is 90 ng/mL or greater.

In another preferred aspect of the invention, the alpha-fetoprotein level is 100 ng/mL or greater.

In another preferred aspect of the invention, the alpha-fetoprotein level is 110 ng/mL or greater.

In another preferred aspect of the invention, the alpha-fetoprotein level is 120 ng/mL or greater.

In another preferred aspect of the invention, the alpha-fetoprotein level is 130 ng/mL or greater.

In another preferred aspect of the invention, the alpha-fetoprotein level is 140 ng/mL or greater.

In another preferred aspect of the invention, the alpha-fetoprotein level is 150 ng/mL or greater.

In another preferred aspect of the invention, the alpha-fetoprotein level is 160 ng/mL or greater.

In another preferred aspect of the invention, the alpha-fetoprotein level is 170 ng/mL or greater.

In another preferred aspect of the invention, the alpha-fetoprotein level is 180 ng/mL or greater.

In another preferred aspect of the invention, the alpha-fetoprotein level is 190 ng/mL or greater.

In another preferred aspect of the invention, the alpha-fetoprotein level is 200 ng/mL or greater.

In another preferred aspect of the invention, the alpha-fetoprotein level is 210 ng/mL or greater.

In another preferred aspect of the invention, the alpha-fetoprotein level is 220 ng/mL or greater.

In another preferred aspect of the invention, the alpha-fetoprotein level is 230 ng/mL or greater.

In another preferred aspect of the invention, the alpha-fetoprotein level is 240 ng/mL or greater.

In another preferred aspect of the invention, the alpha-fetoprotein level is 250 ng/mL or greater.

In another preferred aspect of the invention, the alpha-fetoprotein level is 260 ng/mL or greater.

In another preferred aspect of the invention, the alpha-fetoprotein level is 270 ng/mL or greater.

In another preferred aspect of the invention, the alpha-fetoprotein level is 280 ng/mL or greater.

In another preferred aspect of the invention, the alpha-fetoprotein level is 290 ng/mL or greater.

In another preferred aspect of the invention, the alpha-fetoprotein level is 300 ng/mL or greater.

In another preferred aspect of the invention, the alpha-fetoprotein level is 310 ng/mL or greater.

In another preferred aspect of the invention, the alpha-fetoprotein level is 320 ng/mL or greater.

In another preferred aspect of the invention, the alpha-fetoprotein level is 330 ng/mL or greater.

In another preferred aspect of the invention, the alpha-fetoprotein level is 340 ng/mL or greater.

In another preferred aspect of the invention, the alpha-fetoprotein level is 350 ng/mL or greater.

In another preferred aspect of the invention, the alpha-fetoprotein level is 360 ng/mL or greater.

In another preferred aspect of the invention, the alpha-fetoprotein level is 370 ng/mL or greater.

In another preferred aspect of the invention, the alpha-fetoprotein level is 380 ng/mL or greater.

In another preferred aspect of the invention, the alpha-fetoprotein level is 390 ng/mL or greater.

In another preferred aspect of the invention, the alpha-fetoprotein level is 400 ng/mL or greater.

In another preferred aspect of the invention, the sample is plasma or serum.

In another preferred aspect of the invention, the ramucirumab is administered at a dose of about 8 mg/kg.

As used herein, the term "ramucirumab," also known as IMC-1121B, refers to an anti-VEGFR2 antibody comprising: two heavy chains, each with the amino acid sequence of SEQ ID NO:1, and two light chains, each with the amino acid sequence of SEQ ID NO: 2.

As used herein, the term "antibody" includes immunoglobulin molecules comprising four polypeptide chains: two heavy (H) chains and two light (L) chains inter-connected by disulfide bonds. Individual chains can fold into domains having similar sizes (110-125 amino acids) and structures, but different functions.

The light chain can comprise one variable domain ("VL") and/or one constant domain (abbreviated herein as "CL"). The light chains of human antibodies (immunoglobulins) are either kappa (K) light chains or lambda (λ) light chains. The expression VL, as used herein, is intended to include both the variable regions from kappa-type light chains (VK) and from lambda-type light chains (Vλ). The heavy chain can also comprise one variable domain (VH) and/or, depending on the class or isotype of antibody, three or four constant domains (CH1, CH2, CH3 and CH4) (abbreviated herein collectively as "CH"). In humans, the isotypes are IgA, IgD, IgE, IgG, and IgM, with IgA and IgG further subdivided into subclasses or subtypes ($IgA_{1-2}$ and $IgG_{1-4}$). The present invention includes antibodies of any of the aforementioned classes or subclasses. Human $IgG_1$ is the preferred isotype for the antibodies of the present invention.

Three regions, called hypervariable or complementarity-determining regions (hereinafter "CDRs"), are found in each of VL and VH, which are supported by less variable regions called frameworks (hereinafter "FR"). Amino acids are assigned to a particular CDR region or domain in accordance with various conventions including, but not limited to: Kabat (Kabat, et al., Sequences of Proteins of Immunological Interest, Fifth Edition, U.S. Department of Health and Human Services, NIH Publication No. 91-3242 (1991)); Chothia (Chothia, et al., J Mol Biol. 196:901-917 (1987); Chothia, et al., Nature 342(21): 877-883 (1989)), and/or Oxford Molecular AbM antibody modelling 20 software. Each VH and VL is composed of three CDRs and four FRs, arranged from amino-terminus to carboxy-terminus in the following order: FR1-CDR1-FR2-CDR2-FR3-CDR3-FR4. The portion of an antibody consisting of VL and VH domains is designated Fv (fragment variable) and constitutes the antigen-binding site.

As used herein, the terms "treating," "treat," or "treatment" refer to restraining, slowing, lessening, reducing, or reversing the progression or severity of an existing symptom, disorder, condition, or disease, or ameliorating clinical symptoms of a condition. Beneficial or desired clinical results include, but are not limited to, alleviation of symptoms, diminishment of the extent of a disease or disorder, stabilization of a disease or disorder (i.e., where the disease or disorder does not worsen), delay or slowing of the progression of a disease or disorder, amelioration or palliation of the disease or disorder, and remission (whether partial or total) of the disease or disorder, whether detectable or undetectable. Treatment can also mean prolonging survival as compared to expected survival if not receiving treatment. Those in need of treatment include those already with the disease. In one embodiment, the present invention can be used as a medicament.

As used herein, the term "cancer" refers to or describes the physiological condition in mammals that is typically characterized by unregulated cell growth. Included in this definition are benign and malignant cancers.

In the methods of the present invention, a therapeutically effective amount of an antibody of the invention is administered to a mammal or patient in need thereof. Additionally, the pharmaceutical compositions of the invention may include a therapeutically effective amount of ramucirumab of the invention.

A "therapeutically effective amount," refers to an amount effective, at dosages and for periods of time necessary, to achieve the desired therapeutic result. A therapeutically effective amount can be readily determined by the attending diagnostician, as one skilled in the art, by the use of known techniques and by observing results obtained under analogous circumstances. In determining the therapeutically effective amount for a patient, a number of factors are considered by the attending diagnostician, including, but not limited to: the species of patient; its size, age, and general health; the specific disease or disorder involved; the target site; the degree of the severity of the disease or disorder; the response of the individual patient; the particular compound administered; the mode of administration; the bioavailability characteristics of the preparation administered; the dose regimen selected; the use of concomitant medication; other medications administered; and other relevant circumstances. A therapeutically effective amount is also one in which any toxic or detrimental effects of the antibody or antibody portion are outweighed by the therapeutically beneficial effects.

Generally, dosage regimens may be adjusted to provide the optimum desired response (e.g., a therapeutic response). Treatment dosages may be titrated using routine methods known to those of skill in the art to optimize safety and efficacy. Dosing schedules will typically range from a single bolus dosage or continuous infusion, to multiple administrations per day (e.g., every 4-6 hours), or as indicated by the treating physician and the patient's condition. Dosing frequencies of the antibody will be determined by the physicians treating the patient and may be given daily, three times per week, weekly, every two weeks, or less often, and more preferably every two-weeks. Dosing amounts of the antibody will also be determined by the physicians treating the patient and may fall within customary ranges, more preferably about 8 mg/kg.

In some instances, dosage levels below the lower limit of the aforesaid dosing for ramucirumab may be more than adequate, while in other cases larger doses may be employed with acceptable side effects, and therefore the above dosage amount is not intended to limit the scope of the invention in any way.

The therapeutically effective amount of the treatment of the invention can be measured by various endpoints commonly used in evaluating cancer treatments, including, but not limited to: extending survival (including OS and PFS); resulting in an objective response (including a CR or a PR); tumor regression, tumor weight or size shrinkage, longer time to disease progression, increased duration of survival, longer PFS, improved OS rate, increased duration of response, and improved quality of life and/or improving signs or symptoms of cancer.

As used herein, the term "progressive disease" (PD) refers to least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm The appearance of one or more new lesions is also considered progression.

As used herein, the term "partial response," (PR) refers to at least a 30% decrease in the sum of diameters of target lesions, taking as reference the baseline sum diameters.

As used herein, the term "complete response" (CR) refers to the disappearance of all non-nodal target lesions with the short axes of any target lymph nodes reduced to <10 mm.

As used herein, the term "stable disease" (SD) refers to neither sufficient shrinkage for PR nor sufficient increase to qualify for PD, taking as reference the smallest sum of diameters while on study.

As used herein, the term "objective response rate" (ORR) is equal to the proportion of patients achieving a best overall response of partial or complete response (PR+CR) according to RECIST 1.1.

As used herein, the term "overall survival" (OS) refers to the percentage of patients remaining alive for a defined period of time, such as 1 year, 5 years, etc. from the time of diagnosis or treatment. In a preferred embodiment, OS refers to the time from the date of randomization in the Study to the date of death from any cause. If the patient is alive at the end of the follow-up period or is lost to follow-up, OS data is censored on the last date the patient is known to be alive. Overall survival is evaluated by the Kaplan-Meier method, and a 95% confidence interval (CI) is provided for the median OS in each treatment arm.

As used herein, the term "progression-free survival" (PFS) refers to the patient remaining alive without the cancer progressing or getting worse. In a preferred aspect of the invention, PFS is defined as the time from randomization in the Study until the first radiographic documentation of objective progression as defined by RECIST (Version 1.1), or death from any cause. Patients who die without a reported prior progression will be considered to have progressed on the day of their death. Patients who did not progress or are lost to follow-up will be censored at the day of their last radiographic tumor assessment.

As used herein, the term "disease control rate" (DCR) refers to lack of disease progression and rate thereof. It refers to the group of patients with a best overall response categorized as CR, PR or SD (specifically excluding the patients with PD), wherein the best overall response is the best response recorded from the start of treatment until PD.

As used herein, the term "clinical benefit rate," refers to SD or better at 12 weeks. The tumor response rate of SD or better (i.e. CR+PR+SD) at 12 weeks is defined as the proportion of patients with a response of SD or better, as defined by RECIST 1.1, at 12 weeks following the first dose of study therapy. Patients will be considered "failure" if they die or if radiographic evaluation indicates a response of PD at 12 weeks or before.

As used herein, the term "extending survival" or "prolonged survival" which are used interchangeably herein, is meant as increasing OS or PFS in a treated patient relative to i) an untreated patient, ii) a patient treated with less than all of the anti-tumor agents in a particular combination therapy, or iii) a control treatment protocol. Survival is monitored following the initiation of treatment or following the initial diagnosis of cancer.

As used herein, the term "Upper Limit of Normal" (ULN) is meant to identify the top of a normal range as measured by a laboratory. and can vary per laboratory, though an AFP of 10 ng/mL is a typical value for the ULN used by laboratories in this Study.

Child-Pugh score is a scoring system used to characterize chronic liver disease, mainly cirrhosis. Patients may be considered to have Child-Pugh Class A, B, or C scores, in which a Class A score indicates relatively normal liver function and a score of C indicates severe liver dysfunction.

In the present invention, any suitable method or route can be used to administer ramucirumab of the invention; intravenous (i.v.) administration is the preferred route. It should be emphasized, however, that the present invention is not limited to any particular method or route of administration.

The ramucirumab of the invention, where used in a patient for the purpose of treatment, is preferably formulated as a pharmaceutical composition. Such pharmaceutical compositions and processes for preparing the same are well known in the art. See, e.g. Remington: The Science and Practice of Pharmacy (Gennaro A., et aL, eds., 19th ed., Mack Publishing Co., 1995).

EXAMPLES

The following examples further illustrate the invention, but should not be construed to limit the scope of the invention in any way. Detailed descriptions of conventional methods, such as those employed in the construction of vectors and plasmids, the insertion of genes encoding polypeptides into such vectors and plasmids, the introduction of plasmids into host cells, and the expression and determination thereof of genes and gene products can be obtained from numerous publications, including Sambrook, J. et aL, Molecular Cloning: A Laboratory Manual, 2nd ed., Cold Spring Harbor Laboratory Press (1989) and Coligan, J. et al. Current Protocols in Immunology, Wiley & Sons, Incorporated (2007).

TABLE 1

Amino Acid Sequence of ramucirumab Heavy and Light Chain

|  | Heavy Chain | SEQ ID NO. | Light Chain | SEQ ID NO. |
| --- | --- | --- | --- | --- |
| Full Length | EVQLVQSGGGLV KPGGSLRLSCAA SGFTFSSYSMNW VRQAPGKGLEWV SSISSSSSYIYY ADSVKGRFTISR DNAKNSLYLQMN SLRAEDTAVYYC ARVTDAFDIWGQ GTMVTVSSASTK GPSVLPLAPSSK STSGGTAALGCL VKDYFPEPVTVS WNSGALTSGVHT FPAVLQSSGLYS LSSVVTVPSSSL GTQTYICNVNHK PSNTKVDKRVEP KSCDKTHTCPPC PAPELLGGPSVF LFPPKPKDTLMI SRTPEVTCVVVD VSHEDPEVKFNW YVDGVEVHNAKT KPREEQYNSTYR VVSVLTVLHQDW LNGKEYKCKVSN KALPAPIEKTIS KAKGQPREPQVY TLPPSREEMTKN QVSLTCLVKGFY PSDIAVEWESNG QPENNYKTTPPV LDSDGSFFLYSK | 1 | DIQMTQSPSSVS ASIGDRVTITCR ASQGIDNWLGWY QQKPGKAPKLLI YDASNLDTGVPS RFSGSGSGTYFT LTISSLQAEDFA VYFCQQAKAFPP TFGGGTKVDIKR TVAAPSVFIFPP SDEQLKSGTASV VCLLNNFYPREA KVQWKVDNALQS GNSQESVTEQDS KDSTYSLSSTLT LSKADYEKHKVY ACEVTHQGLSSP VTKSFNRGEC | 2 |

TABLE 1-continued

Amino Acid Sequence of ramucirumab
Heavy and Light Chain

| Heavy Chain | SEQ ID NO. | Light Chain | SEQ ID NO. |
|---|---|---|---|
| LTVDKSRWQQGN<br>VFSCSVMHEALH<br>NHYTQKSLSLSP<br>GK | | | |

A Multicenter, Randomized, Double-Blind, Phase 3 Study of Ramucirumab (IMC-1121B) Drug Product and Best Supportive Care (BSC) Versus Placebo and BSC as Second-Line Treatment in Patients with Hepatocellular Carcinoma Following First-Line Therapy With Sorafenib.

Study Design:

The Study is A Multicenter, Randomized, Double-Blind, Phase 3 Study of Ramucirumab (IMC-1121B) Drug Product and Best Supportive Care (BSC) Versus Placebo and BSC as Second-Line Treatment in Patients with Hepatocellular Carcinoma Following First-Line Therapy With Sorafenib.

Approximately 544 enrolled patients with Child-Pugh Class A score at baseline who meet all eligibility criteria are randomized into two Arms. Arm A patients receive Ramucirumab (IMC-1121B) Drug Product (DP) and Best Supportive Care (BSC) and Arm B patients receive placebo and BSC. At randomization, patients are stratified by geographic region (North America vs Europe vs East Asia), and etiology of liver disease (hepatitis B vs hepatitis C vs other etiologies). Ramucirumab DP is a sterile, preservative-free solution for infusion and is formulated in an aqueous solution at a concentration of 10 mg/mL (500 mg/50-mL vial), administered as an intravenous (I.V.) infusion at a dose of 8 mg/kg every 2 weeks. The infusion is delivered in approximately 60 minutes. The infusion rate does not exceed 25 mg/minute. Placebo drug product is a sterile, preservative-free solution for infusion containing histidine buffer only. The volume of placebo drug product administered is calculated as if it were active product formulated in an aqueous solution at a concentration of 10 mg/mL (500 mg/50-mL vial) (with a dose of 8 mg/kg). The first dose of ramucirumab DP (or placebo) is dependent upon the patient's baseline body weight in kilograms. Subsequent doses of ramucirumab DP (or placebo) must be recalculated if there is a ≥10% change (increase or decrease) in body weight from last dose calculation; subsequent doses may be recalculated if there is a <10% change (increase or decrease) in body weight from last dose calculation.

A treatment cycle is defined as 2 weeks, with radiologic evaluation every 6 weeks (±3 days) after first dose of study therapy for the first 6 months, and every 9 weeks (±3 days) thereafter. There is no planned interruption between treatment cycles. The treatment regimen is continued until radiographic progression or symptomatic deterioration characterized as progression of disease, the development of unacceptable toxicity, noncompliance or withdrawal of consent by the patient, or investigator decision.

Efficacy Analysis:

Final analysis is performed after 438 OS events are observed in HCC patients with Child-Pugh Class A score. In addition, an interim analysis for unequivocal efficacy is performed after approximately 328 OS events; if unequivocal efficacy is declared, then this interim analysis constitutes the final inferential analysis of OS, and any subsequent analysis based on a larger number of OS events are considered exploratory.

The end of trial occurs when Study completion has occurred and the last patient has discontinued study treatment and completed the 30-Day Safety Follow-up visit (and any AEs that are serious or considered related to study treatment or that caused discontinuation of treatment are followed until the event is resolved, stabilized, returned to baseline, is deemed irreversible, or otherwise been explained).

The primary efficacy endpoint is Overall Survival (OS). The secondary efficacy endpoints are Progression-free survival (PFS), Objective response rate (ORR), Time to radiographic progression (TTP), Patient-reported outcomes (PRO) based on FHSI-8 and EQ-5D.

Tumor measurements are done by CT scan or equivalent and assessed according to Response Evaluation Criteria in Solid Tumors, Version 1.1 (RECIST v 1.1). Despite any treatment delays, the imaging studies are collected approximately every 6 weeks (±3 days) after first dose for the first 6 months, and every 9 weeks (±3 days) thereafter.

Overall survival is defined as the time from the date of randomization to the date of death from any cause. If the patient is alive at the end of the follow-up period or is lost to follow-up, OS data is censored on the last date the patient is known to be alive. Overall survival is evaluated by the Kaplan-Meier method, and a 95% confidence interval (CI) is provided for the median OS in each treatment arm.

The primary analysis compares the observed OS between the 2 treatment arms (ramucirumab DP plus BSC versus placebo plus BSC). The primary analysis is conducted in the ITT population (patients with Child-Pugh Class A score). The comparison uses the log-rank test, stratified by randomization stratification factors: geographic region (North America vs Europe vs East Asia, where the stratification label "North America" comprises countries from North America and South America; the label "Europe" comprises countries from Europe, Israel, Australia, and New Zealand; and the label "East Asia" comprises countries from Asia, except for Israel), and etiology of liver disease (hepatitis B vs hepatitis C vs other etiologies). A sensitivity analysis may be performed using the etiology of liver disease reported on the eCRF. An additional analysis with an unstratified log-rank test is also performed. The estimation of the survival curves for the 2 treatment groups is generated using the Kaplan-Meier methodology. A stratified Cox proportional hazards regression model to compare the treatments within the clusters defined by the stratifying variables is also performed to generate the hazard ratio (HR). An additional unstratified Cox regression model is employed to explore the effects of prognostic variables, including the stratification variables and additional factors (eg, presence of macrovascular invasion, extrahepatic spread, BCLC stage, presence vs absence of histologic confirmation of diagnosis, and prior treatment with sorafenib [including duration of treatment and reasons for discontinuation]), on treatment efficacy. The primary statistical analysis is conducted in the Child-Pugh Class A population only and includes all randomized patients with Child-Pugh Class A score at baseline. Overall survival, PFS, and time to radiographic progression is evaluated by the Kaplan-Meier method with a 95% confidence interval (CI) for the median time. The primary analysis compares the OS observed with ramucirumab DP (plus BSC) versus placebo (plus BSC); the 2 arms are compared using a stratified log-rank test. ORR is presented with a 2-sided 95% CI, with best overall response (classified according to RECIST v 1.1 or similar guidelines) summarized by frequency and percentage. The ORR in each treatment group is compared using the Cochran-Mantel-Haenszel test adjusted for the stratification variables.

FHSI-8 scores and their change from baseline are summarized descriptively at each assessment time point. The change from baseline in FHSI-8 is compared to determine whether statistically significant differences exist between the ramucirumab DP and placebo arms. The EQ-5D data is scored as an index where 0=death and 1=perfect health, using the UK weighting algorithm. The visual analogue scale (VAS) are scored from 0 (worst imaginable health state) through 100 (best imaginable health state).

Survival follow-up is conducted after discontinuation of study therapy, every 2 months ±7 days for as long as the patient is alive, but not beyond study completion. (Survival follow-up is not conducted for patients on the extension period of the study.)

Results:

A total of 565 patients, who met all eligibility criteria, were randomized into the two treatment arms. The primary efficacy endpoint of OS in the ramucirumab DP arm versus placebo arm resulted in a median OS of 9.17 months (95% CI=8.05, 10.64) and 7.62 months (95% CI=6.01, 9.33) respectively. The stratified HR for this analysis was 0.866 (95% CI=0.717, 1.046) with a stratified Log-rank p-value of p=0.1391. Although the p-value did not reach statistical significance, the HR of 0.866 represents a 13% reduction in the risk of death for patients receiving ramucirumab. These results indicate a trend for improvement in survival in the ramucirumab arm compared to the placebo arm.

The median PFS in the ramucirumab DP arm and the placebo arm was 2.8 months (95% CI=2.7, 3.9) and 2.1 months (95% CI=1.6, 2.7) respectively. The stratified HR for this analysis was 0.625 (95% CI=0.522, 0.750) with a stratified Log-rank p-value of p<0.0001. The 6-month and 9-month PFS rates for the ramucirumab arm were 32.1% and 20.7%, respectively, and the 6-month and 9-month PFS rates for the placebo arm were 12.9% and 8.3%, respectively. These results demonstrate that ramucirumab has a meaningful impact on PFS, by more than doubling the PFS rates at 6 and 9 months when compared with placebo.

The time to progression (TTP) in the ramucirumab DP treatment arm and placebo treatment arm resulted in 3.48 months (95% CI=2.8, 4.5) and 2.63 months (95% CI=1.6, 2.8), respectively. The stratified HR for this analysis was 0.593 (95% CI=0.487, 0.722) with a stratified Log-rank p-value of <0.0001. The 6-month and 9-month TTP rates for the ramucirumab arm were 37.0% and 27.0%, respectively, and the 6-month and 9-month TTP rates for the placebo treatment arm were 14.9% and 10.8%, respectively. These results demonstrate that ramucirumab has a meaningful impact on TTP, more than doubling the progression-free rates at 6 and 9 months compared with placebo.

The overall response rate (complete response+partial response) in the ramucirumab arm and placebo arm was 7.1% (95% CI=4.6, 10.7) and 0.7% (95% CI=0.2, 2.5), respectively, with a p-value of <0.0001 using the Cochran-Mantel-Haenszel test adjusted for randomization strata. These results show a 10-fold improvement in ORR in the ramucirumab arm when compared to the placebo arm. The disease control rates (complete response+partial response+ stable disease) in the ramucirumab arm and placebo arm were 56.2% (95% CI=50.4, 61.8) and 45.7% (95% CI=40.0, 51.6), respectively, with a p-value of 0.0110 using the same test for overall response rate.

The secondary endpoints PFS, TTP and ORR demonstrate the benefit of ramucirumab DP as second-line treatment in patients with HCC following first-line therapy with sorafenib.

Association of Baseline Alpha-Fetoprotein (AFP) and Observed Treatment Effect for Ramucirumab:

A poorer prognosis for HCC patients is associated with elevated AFP, macro-vascular invasion, and higher stage of disease (i.e., extrahepatic metastases), increased micro-vessel density and increased VEGF expression. The elevated AFP population in this trial shares several of these factors.

When evaluating OS in the placebo arm, patients with AFP levels greater than 400 ng/mL have a worse prognosis than patients with AFP levels less than or equal to 400ng/mL. This indicates that AFP is a prognostic factor for OS in HCC patients.

A pre-specified subgroup analysis was performed in the ITT population with baseline AFP<400 (310 patients) or ≥400 ng/mL (250 patients). In patients with a baseline AFP≥400 ng/mL, the median OS in the ramucirumab arm was 7.8 months, and the median OS in the placebo arm was 4.2 months. An unexpected improvement of 3.6 months was observed. The stratified HR was 0.674 (95% CI: 0.508, 0.895; p=0.0059), indicating a reduction in the risk of death by 32.6%. No improvement in median OS was observed in patients with a baseline AFP<400 ng/mL. In patients with a baseline AFP<400 ng/mL, the median OS in the ramucirumab arm was 10.1 months, and the median OS in the placebo arm was 11.8 months. The stratified HR was 1.093 (95% CI: 0.836, 1.428; p =0.5059). Baseline AFP and ramucirumab treatment demonstrated a significant subgroup-by-treatment interaction on OS HR with a p=0.0272.

A pre-specified subgroup analysis of PFS in the Ramucirumab DP arm was performed in the patient populations defined by an alpha-fetoprotein (AFP) serum level ≥or <400 ng/mL. In the population with a baseline AFP ≥400 ng/mL, the PFS HR was 0.691 (95% CI: 0.530, 0.901) (p=0.0106), and in the population with a baseline AFP <400 ng/mL, the PFS HR was 0.645 (95% CI: 0.506, 0.821) (p<0.0001). The comparable PFS results observed in patient populations with a baseline AFP≥and <400 ng/mL suggest ramucirumab has antitumor activity irrespective of baseline AFP.

The benefit of ramucirumab was further assessed in the Study patient populations defined by a baseline AFP<or ≥1.5×Upper Limit of Normal (ULN). ULN AFP levels for these analyses is determined separately by each laboratory, though an AFP of 10 ng/mL is a typical value for the ULN used by local laboratories in this Study. Analysis of HR and median survival times was performed to assess the relationship between baseline AFP and the observed OS results.

In patients with AFP levels ≥1.5×ULN, the median OS in the ramucirumab arm was 8.6 months (95% CI: 7.2, 10.1), and the median OS in the placebo arm was 5.7 months (95% CI: 4.7, 7.0) with a stratified HR of 0.749 (CI: 0.603, 0.930) and stratified Log-rank p-value of p=0.0088. A median OS improvement of 2.9 months was observed; a survival improvement that is similar in magnitude to that observed in patients with AFP levels ≥400 ng/mL. Subgroup-by-treatment interaction testing for a baseline AFP<or ≥1.5×ULN with the OS treatment effect demonstrated a p-value of 0.0372. The results indicate that the survival benefit observed in the pre-specified analyses may be extended to patients with modestly elevated baseline AFP.

In patients with an AFP<1.5×ULN, the median OS in the ramucirumab arm was 11.6 months compared to 16.4 months for the placebo arm. The stratified HR was 1.337 (95% CI: (0.874, 2.046)), with a p-value of 0.1789. Thus, the population defined by a baseline AFP<1.5×ULN identifies the subgroup unlikely to derive an OS benefit from ramucirumab treatment.

More surprisingly, for patient populations with a baseline AFP≥10 ng/mL or any higher threshold, the difference in median OS between the ramucirumab and placebo treatment arms is maintained at approximately 3 months, despite the fact that the absolute survival times become progressively shorter in populations defined by increasing thresholds of AFP. In addition, patient populations with a baseline AFP≥10 ng/mL or any higher threshold, the p-value associated with the HR is p<0.05 over a range of AFP values where the confidence in the results is not limited by sample size. For patient populations with a baseline AFP≥10 ng/mL or any higher threshold the HRs are in the range of approximately 0.50 to 0.75, becoming generally more favorable with increasing thresholds of AFP.

A robust and clinically meaningful improvement in OS, comparing the ramucirumab arm with the placebo arm, was observed using both AFP threshold values, AFP≥400 ng/mL and AFP≥1.5×ULN. This survival improvement was consistently 3 months, even in the patient population with poor prognosis HCC and highly elevated (≥400 ng/mL) levels of baseline AFP. These results demonstrate the consistent predictive value of an elevated baseline AFP for ramucirumab treatment.

We claim:

1. A method of selecting a patient having a hepatocellular tumor and treating said patient with a therapeutically effective amount of ramucirumab, comprising assaying for the level of alpha-fetoprotein in a plasma or serum sample taken from the patient, and selecting and treating the patient with a therapeutically effective amount of ramucirumab if the level of alpha-fetoprotein in the sample is 400 ng/mL or greater.

2. The method of claim 1, wherein the sample is serum.

3. The method of claim 1, wherein the sample is plasma.

4. The method of claim 1, wherein ramucirumab is administered at a dose of about 8 mg/kg, every two weeks.

5. The method of claim 1, wherein the patient was previously treated with sorafenib.

6. A therapeutic regimen for treating a patient with a hepatocellular tumor, comprising: (1) assaying for the level of alpha-fetoprotein in a plasma or serum sample taken from the patient, (2) selecting the patient for treatment with ramucirumab if the level of alpha-fetoprotein in the sample is 400 ng/mL or greater, and (3) administering ramucirumab to the patient if the level of alpha-fetoprotein in the sample is 400-ng/mL or greater.

7. The method of claim 6, wherein the sample is serum.

8. The method of claim 6, wherein the sample is plasma.

9. The method of claim 6, wherein ramucirumab is administered at a dose of about 8 mg/kg, every two weeks.

10. The method of claim 6, wherein the patient was previously treated with sorafenib.

11. A method of treating a hepatocellular tumor in a selected patient, comprising selecting the patient if a serum or plasma sample taken from the patient has an alpha-fetoprotein level of 400 ng/mL or greater, and administering a therapeutically effective amount of ramucirumab to the patient, selected as having a level of alpha-fetoprotein of 400 ng/mL or greater in the serum or plasma sample taken from the patient.

12. The method of claim 11, wherein the sample is serum.

13. The method of claim 11, wherein the sample is plasma.

14. The method of claim 11, wherein the ramucirumab is administered at a dose of about 8 mg/kg, every two weeks.

15. The method of claim 11, wherein the patient was treated with sorafenib prior to administration of ramucirumab.

16. A method of treating a hepatocellular tumor in a selected patient, comprising selecting the patient if a serum or plasma sample taken from the patient has an alpha-fetoprotein level of 400 ng/mL or greater, and administering a therapeutically effective amount of an anti-VEGFR2 antibody to the patient selected as having a level of alpha-fetoprotein of 400 ng/mL or greater in the serum or plasma sample taken from the patient, wherein the anti-VEGFR2 antibody comprises two heavy chains, each with the amino acid sequence of SEQ ID NO: 1, and two light chains, each with the amino acid sequence of SEQ ID NO: 2.

17. The method of claim 16, wherein the sample is serum.

18. The method of claim 16, wherein the sample is plasma.

19. The method of claim 16, wherein the anti-VEGFR2 antibody is administered at a dose of about 8 mg/kg, every two weeks.

20. The method of claim 16, wherein the patient was previously treated with sorafenib.

* * * * *

UNITED STATES PATENT AND TRADEMARK OFFICE
CERTIFICATE OF CORRECTION

PATENT NO. : 10,766,961 B2  
APPLICATION NO. : 15/501507  
DATED : September 8, 2020  
INVENTOR(S) : Paolo B. Abada et al.

Page 1 of 1

It is certified that error appears in the above-identified patent and that said Letters Patent is hereby corrected as shown below:

In the Claims

In Column 17, Line 32, in Claim 6, please delete "400-ng/mL" and insert -- 400 ng/mL --, therefor.

In Column 18, Line 11, in Claim 11, please delete "patient," and insert -- patient --, therefor.

Signed and Sealed this  
Ninth Day of February, 2021

Drew Hirshfeld  
*Performing the Functions and Duties of the*  
*Under Secretary of Commerce for Intellectual Property and*  
*Director of the United States Patent and Trademark Office*